US 6,605,752 B2

(12) United States Patent
Magnusson et al.

(10) Patent No.: US 6,605,752 B2
(45) Date of Patent: Aug. 12, 2003

(54) ABSORBENT PRODUCT WITH IMPROVED INSTANTANEOUS LIQUID ADSORPTION, AND IMPROVED FIT

(75) Inventors: Ing-Britt Magnusson, Mölnlycke (SE); Lennart Nilsson, Skärhamn (SE)

(73) Assignee: SCA Hygiene Products AB, Gothenburg (SE)

( * ) Notice: Subject to any disclaimer, the term of this patent is extended or adjusted under 35 U.S.C. 154(b) by 81 days.

(21) Appl. No.: 09/984,553

(22) Filed: Oct. 30, 2001

(65) Prior Publication Data

US 2002/0052587 A1 May 2, 2002

Related U.S. Application Data

(60) Provisional application No. 60/244,204, filed on Oct. 31, 2000.

(30) Foreign Application Priority Data

Oct. 30, 2000 (SE) .............................................. 0003937

(51) Int. Cl.[7] .................................................. A61F 13/15
(52) U.S. Cl. ..................... 604/379; 604/359; 604/367; 604/368; 604/378; 604/385.01; 604/385.23
(58) Field of Search ................................. 604/359, 367, 604/368, 378, 379, 385.01, 385.23

(56) References Cited

U.S. PATENT DOCUMENTS 4,781,710 A    11/1988  Megison et al.
6,447,494 B1 *  9/2002  Kashiwagi et al. ..... 604/385.03
6,462,253 B1 * 10/2002  Magnusson et al. ........ 604/378

FOREIGN PATENT DOCUMENTS

EP    1 008 333    6/2000
EP    1 048 278   11/2000
WO    WO 00/32147  6/2000

* cited by examiner

Primary Examiner—A. Vanatta
Assistant Examiner—Angela J Grayson
(74) Attorney, Agent, or Firm—Young & Thompson

(57) ABSTRACT

An absorbent product which possesses two longitudinal side edges (12,13), two transverse end edges (10,11), a longitudinal centre line and a transverse centre line, and which comprises a liquid-permeable outer layer (2), a liquid-impermeable backing layer (3) and an absorption core (4) which is located between the outer layer (2) and the backing layer (3), with the absorption core (4) comprising a first and a second absorption layer (14,15), with the first absorption layer (14) being arranged behind the liquid-permeable outer layer (2) and the second absorption layer (15) being arranged between the first absorption layer (14) and the liquid-impermeable backing layer (3), with the first absorption layer (14) having two longitudinal channels (16,17), with each of the channels having an outer edge (20) closest to the corresponding longitudinal side edge (12,13) of the product and an inner edge (21) closest to the longitudinal centre line of the product. The two longitudinal channels (16,17) extend through the whole of the thickness of the first absorption layer (14), and a compressed area (22) is arranged between the longitudinal sides (12,13) of the absorbent product, wherein the distance between the side edges (24) of the compressed area (22) is smaller than or equal to the distance between the outer side edges (20) of the longitudinal channels (16,17).

18 Claims, 2 Drawing Sheets

ABSORBENT PRODUCT WITH IMPROVED INSTANTANEOUS LIQUID ADSORPTION, AND IMPROVED FIT

TECHNICAL FIELD

An absorbent product which possesses two longitudinal side edges, two transverse end edges, a longitudinal centre line and a transverse centre line, and which comprises a liquid-permeable outer layer, a liquid-impermeable backing layer and an absorption core which is located between the said outer layer and the said backing layer, with the said absorption core comprising a first and a second absorption layer, with the first absorption layer being arranged behind the liquid-permeable outer layer and the second absorptive layer being arranged between the first absorption layer and the liquid-impermeable backing layer, with the first absorption layer having two longitudinal channels, with each of the channels having an outer edge closest to the corresponding longitudinal side edge of the product and an inner edge closest to the longitudinal centre line of the product.

BACKGROUND

A problem with absorbent products is that of ensuring that they do not leak. Leakage is not usually due to the total absorptive capacity of the product being insufficient. Instead, the reason for the leakage can, for example, be that released liquid ends up outside the absorption body due to the product having come to be located in an incorrect position when being put on or as a consequence of stresses during use, or that the product has been deformed such that the surface available for liquid absorption has become insufficient. Another common reason for leakage is that the liquid runs along the surface of the product without being absorbed due to the product exhibiting low instantaneous liquid absorption or having been deformed in an undesirable manner when being used.

It has been previously known, from U.S. Pat. No. 4,655,759, to provide an absorbent product with compressed, arcuated channels which are arranged in the longitudinal direction of the absorption core. The compressed channels are stated to assist the article in forming the shape of a W in cross-sectional profile when the article is pressed together by the thighs of the user. The improved fit is said to minimize the risk of leakage. Beyond the compressed channels, in the direction towards the rearside, i.e. in that part of the product which is arranged, during use, closest to the back and the caudal vertebra, the cross-sectional profile is changed to an inverted V shape. This is said to make it possible to achieve a better fit between the buttocks of the user.

WO 95/15139 attempts to solve the problem of lateral leakage by means of compressed channels which shape the absorbent article into a container for the liquid when the article is used. In addition, the channels help the article to distance itself somewhat from the user. WO 90/14814 uses sewn or glued channels in order to obtain an effect of upturned edges which is said to protect against lateral leakage. EP 0,249,405 uses compressed, arcuate longitudinal channels on each side of an elevation on the core. In addition, the channels can extend further to compressed areas or be arranged around the whole of the core. This is stated to ensure that full contact is achieved between the user and the article and to prevent lateral leakage.

However, the abovementioned inventions fail to identify and indicate a satisfactory way in which all possibilities of leakage can be avoided.

An aim of the present invention is to improve existing efforts to solve the above problem. Another aim of the present invention is to improve instantaneous liquid absorption at the same time as obtaining a good, stable and user-friendly fit and thereby to decrease discomfort, leakage and skin irritations which can arise due to the product chafing the skin.

ACCOUNT OF THE INVENTION

The present invention has been used to achieve an absorbent product of the type mentioned at the outset, which product essentially eliminates the problems associated with previously known products of this nature.

The product which is designed in accordance with the invention is principally distinguished by the fact that the two longitudinal channels extend through the whole of the thickness of the first absorptive layer and that a compressed area is arranged between the longitudinal sides of the absorbent product and that the distance between the side edges of the compressed area is smaller than or equal to the distance between the outer side edges of the longitudinal channels.

The combination of the longitudinal channels and the compressed area between the channels results in high instantaneous liquid absorption, with a good fit at the same time being retained during the dry state. The liquid which the product receives can penetrate rapidly and readily down through the channels to the underlying core, resulting in more rapid admission. The channels also shape the product in conformance with the inside of the user's thighs, resulting in a good U-like fit being achieved. A good fit minimizes leakage which can occur due to occasional gaps which are formed between the absorbent product and the user's body. The compressed area contributes to ensuring a good fit and increases the stability and deformation resistance of the product, thereby helping the absorbent product to remain in place during use. In addition, the second absorptive layer serves to hide the channels so that the latter cannot be seen through the liquid-impermeable backing layer, something which might otherwise be regarded by users as being disturbing and disquieting. A particularly good masking effect is obtained if the compressed area is arranged in the second absorptive layer. A further advantage of the invention is also the fact that substantial economies in material can be obtained due to it being possible to recirculate all the material which has been removed from the channels back to earlier production stages.

The compressed area preferably extends transversely the whole way between the outer edges of the two channels. In addition, the longitudinal extent of the compressed area preferably corresponds essentially to the length of the channels. Alternatively, the length of the compressed area can be greater or less than the length of the channels; for example, the compressed area can extend the whole length of the absorptive body. It is also possible to design the compressed area with straight side edges even if the channels have a curved shape, or vice versa. Moreover, if the compressed area extends past the ends of the channels, the portion or portions of the compressed area being located beyond the channels may have a greater width than the distance between the outer edges of the channels. This situation can occur, for instance, when the channels are curved and the compressed area has curved longitudinal edges which follows the contour of the channels and extend in a curved fashion beyond the ends of the channels. However, preference is given to designing the side edges of the compressed area such that they the have the same general shape as the channels.

According to an alternative embodiment, it is possible to arrange a further two longitudinal arcuate channels in the second absorption layer, with the channels extending through the whole of the thickness of the second absorption layer. The masking effect of the second absorption layer is naturally lost in such an embodiment.

According to one embodiment, the first absorption layer consists of chemical thermomechanical pulp and the second absorption layer consists chemical pulp. Chemical thermomechanical pulp will henceforth be termed CTMP and chemical pulp will henceforth be termed CP. A CTMP layer has a relatively open structure with relatively large capillaries since CTMP fibres are rigid and moderately coarse. To a large extent, the open structure remains even after wetting since the fibres retain much of their rigidity. Consequently, an absorption layer composed of CTMP has a comparatively great ability to take up liquid instantaneously and good ability to retain liquid but a comparatively poor ability to spread liquid.

CP fibres are thin and flexible and form a fibre structure having relatively small capillaries when they are laid in a layer. An absorption layer composed of CP fibres has a great ability to spread liquid; however, because the capillaries are small, absorption into the layer only takes place slowly. It is obviously possible, within the scope of the invention, to conceive of the first absorption layer consisting of CP and the second absorption layer consisting of CTMP.

Different types of absorbent foam, and absorbent bound or unbound fibre structures, consisting entirely or partly of absorbent fibres such as cotton, rayon, peat, flax or the like, are other absorptive materials which can be used when constructing an absorbent product according to the invention. It is furthermore possible for the absorbent product to comprise so-called super absorbents, which are absorbent polymeric materials which are able to absorb many times their own weight of body liquid, thereby forming an aqueous gel. Superabsorbents exist in the form of particles, fibres, flakes, granules or films and can be mixed with other materials in the absorption body or be arranged in separate layers.

According to one embodiment, the first absorption layer is smaller in the longitudinal direction than the second absorption layer. The first absorption layer can also be smaller in the transverse direction than the second absorption layer. This enables the absorption capacity to be optimized to the wetting region, i.e. that part of the product which is expected to be the first to be wetted by liquid.

It is naturally also possible, within the scope of the invention, to conceive of a structure in which the first absorption layer is larger in the longitudinal direction than the second absorptive layer. The first absorption layer can also be larger in the transverse direction than the second absorption layer.

According to another embodiment, the first absorption layer is compressed between the outer edges of the two longitudinal channels, i.e. the edges closest to the longitudinal side edges of the product. A compression in a part of the first absorption layer stabilizes the absorbent product in the dry state. In addition, the total thickness of the absorbent product is reduced and, as a result, the product is not felt to be as uncomfortable as would otherwise be the case.

According to yet another embodiment, the second absorption layer is compressed and the width of the compressed area is smaller than or equal to the distance between the outer edges of the two longitudinal channels. A compression in a part of the second absorption layer, like compression of the first absorption layer, stabilizes the shape in the dry state. It also contributes to the channels not being visible through the liquid-impermeable backing layer, something which can otherwise be regarded by the user as being disturbing and disquieting. Together with the pulp recesses in the first absorption layer, the compressed region creates folding directions for a bowl shape in the crotch part of the product, resulting in the product having a U-like shape during use. It is also possible, within the scope of the invention, to arrange for the compressed area to consist of a separate layer whose transverse extent is smaller than or equal to the distance between the outer edges of the longitudinal channels.

The density of the area of the compressed absorption layer can be 0.1–0.5 g/cm$^3$, preferably 0.14–0.5 g/cm$^3$, and most preferably 0.18–0.3 g/cm$^3$.

According to one embodiment, the first absorption layer contains superabsorbents. The presence of superabsorbents in the first absorption layer provides compensation for the absorptive ability which is lost due to absorptive material being removed when the channels are made. Taken together with the channels, they result in a product exhibiting very high instantaneous liquid absorption.

According to one embodiment, the second absorption layer contains superabsorbents. The presence of superabsorbents in the second absorption layer results in the absorbent product being able to absorb and store large quantities of liquid.

It is naturally also possible, within the scope of the invention, to conceive of a structure in which both the first and the second absorption layers contain superabsorbent. It is also possible, within the scope of the invention, to conceive of a product which contains two or more different types of superabsorbent in the first and/or second absorption layers.

According to one embodiment, the longitudinal channels are arcuate. Arcuate channels contribute to further improving the fit when the product is used. Thus, the channels provide a comfortable and superior fit in addition to permitting high instantaneous liquid absorption. The channels constrain the product to assume a U-like shape when the product is used.

The length of each longitudinal channel is preferably 10–22 cm. This does not rule out the length of the channels being matched to the size of the absorbent product or, for that matter, to the size of the first absorption layer. The distance between the inner edges of each longitudinal channel can vary in the longitudinal direction of the product and is 1.0–9.0 cm, preferably 1.0–7.0 cm, or most preferably 2.0–4.5 cm. It is also possible, within the scope of the invention, to conceive of a structure in which the distance between the inner edges of each longitudinal channel is constant in the longitudinal direction of the product. Naturally, such a channel structure would give rise to arcuate channels. The width of the longitudinal channels is 0.1–1.0 cm.

According to one embodiment, the first absorption layer is 22–25 cm in the longitudinal direction and the second absorption layer is 30–33 cm in the longitudinal direction.

Furthermore, the absorbent product according to the invention can contain at least one odour-inhibiting substrate in the first absorption layer. The second absorption layer can also contain at least one odour-inhibiting substrate. Examples of some of the odour-inhibiting substrates which can be used are zeolites, active charcoal, ion exchangers, different forms of pH-regulating substances, for example acids or partially neutralized superabsorbents, etc.

According to one embodiment, the length of the compressed area is 13–22 cm, preferably 16–20 cm, and most preferably 17–18 cm. The distance between the side edges of the compressed area is 1–8 cm, preferably 3–6.5 cm, and most preferably 4–5.5 cm.

BRIEF DESCRIPTION OF THE FIGURES

The invention will be described below in more detail and with reference to the figures which are shown on the attached drawings.

In this connection.

DESCRIPTION OF EMBODIMENTS

Figure 1:
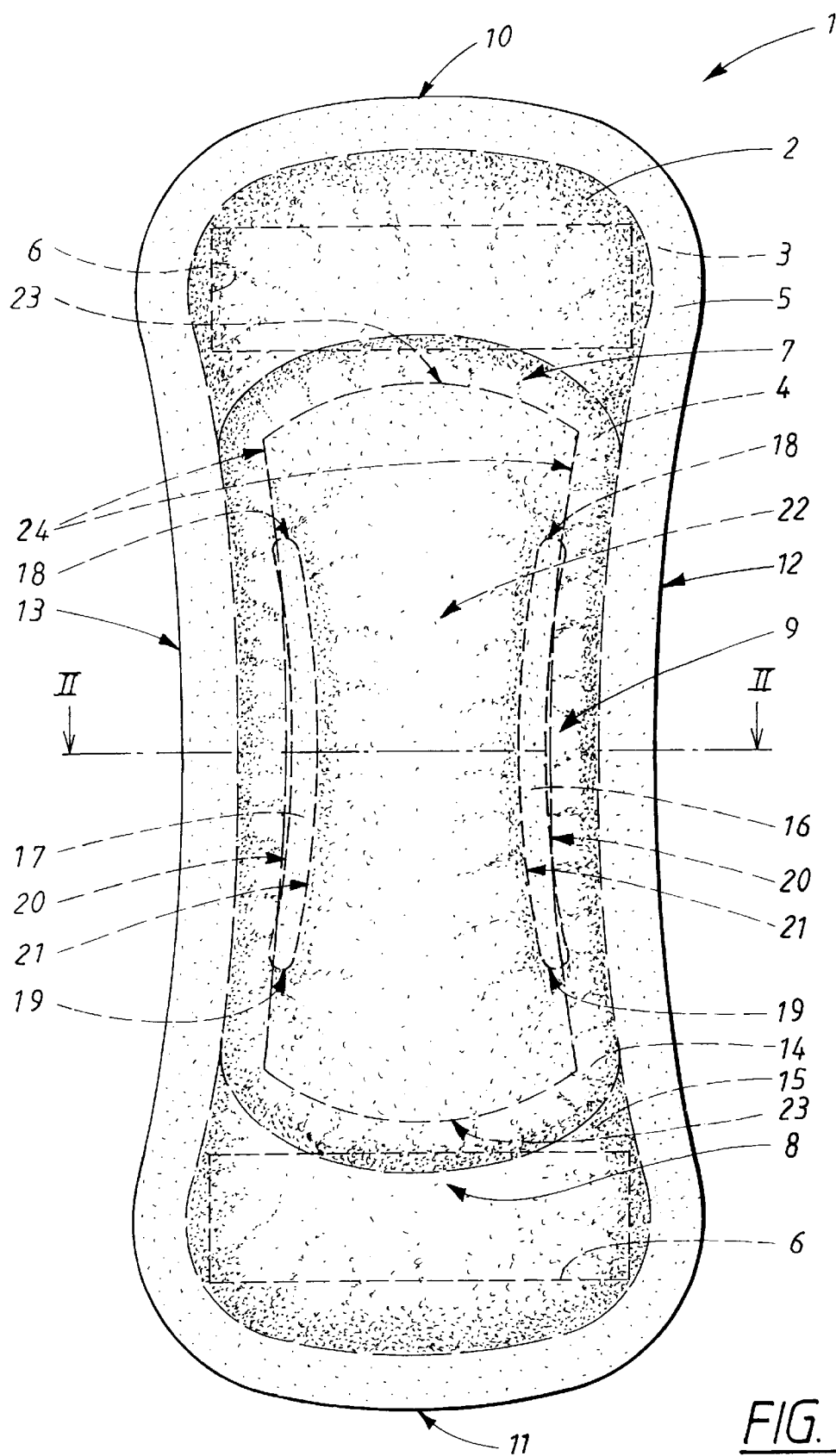
FIG. 1 shows a planar view of an absorbent product, seen from the side which is intended to be facing the user when the product is used.

The product 1 shown in FIG. 1 comprises a first liquid-permeable outer layer 2 and a second liquid-impermeable backing layer 3, and also an absorption body 4 which is enclosed between the layers 2,3. The two layers 2,3 have a somewhat greater extent in the plane than does the absorption body 4 and project past the absorption body 4 around the whole of the periphery of this body. The layers 2,3 are connected to each other within the projecting part 5, for example by means of gluing or welding with heat or ultrasound. The product has a longitudinal centre line and a transverse centre line.

The liquid-permeable outer layer 2 consists, for example, of a layer of nonwoven fibre material or of perforated plastic film, net material or the like. The liquid-impermeable backing layer 3 can consist of a liquid-impermeable plastic film, a nonwoven layer which has been coated with a liquid-blocking material, or some other easily flexed material layer which is able to resist liquid penetration. In general, it is an advantage if the liquid-impermeable backing layer 3 exhibits a certain degree of breathability, i.e. allows water vapour to pass through the layer 3.

A fastening member 6 is arranged, in the form of two transverse regions of self-adhesive glue, on the outer side of the liquid-impermeable backing layer 3. Before use, the fastening member 6 is expediently covered with a detachable protective layer (not shown on the drawing) of release agent-treated paper, plastic film or the like. A number of other glue patterns, such as one or more longitudinal regions, spots, continuous covering, etc., can be used instead of the glue pattern which is shown and which is in the form of two transverse glue regions. Alternatively, it is possible to use other types of fastening member, such as velcro surfaces, press studs, girdles, special underpants, or the like.

An incontinence protection 1 of the type shown in the figures is primarily intended to be used by individuals who are suffering from relatively mild incontinence problems and is therefore of a size which is such that it can easily be accommodated inside a pair of ordinary underpants. In this connection, the fastening member 6 serves to hold the product in place inside the underpants.

The product 1 is in the main shaped like an hourglass, with wider end parts 7,8 and a narrower crotch part 9, which is located between the end parts 7,8. The crotch part 9 is that part of the product 1 which, during use, is intended to be applied to the user's crotch and to serve as the surface for receiving the body liquid which is excreted into the product 1. In addition, the product 1 possesses two transverse, rounded-off end edges 10,11 and also two longitudinal, curved side edges 12,13 running between the end edges 10,11.

The absorption body 4 shown in FIG. 1 consists of at least a first and a second absorption layer 14,15, which are of differing composition and where the first absorption layer 14 is located between the liquid-permeable outer layer 2 and the second absorption layer 15, and the second absorption layer 15 is located between the first absorption layer 14 and the liquid-impermeable backing layer 3. The absorption layers are of differing sizes, with the first absorption layer 14 being smaller than the second absorption layer 15. The first and second absorption layers 14,15 have an appearance which is in the main hour-glass-shaped.

The first absorption layer 14 expediently consists in the main of cellulose fluff pulp which is produced chemithermomechanically and which will henceforth be termed CTMP. A layer of such fluff pulp has a relatively open structure with relatively large capillaries since CTMP fibres are rigid and moderately coarse. To a large extent, the structure remains even after wetting since the fibres retain much of their rigidity. Consequently, an absorption layer 14 consisting of CTMP has a comparatively great ability to take up liquid instantaneously and good ability to retain liquid but a comparatively poor ability to spread liquid.

The second absorption layer 15 expediently consists in the main of cellulose fluff pulp which has been produced chemically and which will henceforth be termed CP. The fibres in such a fluff pulp are thin and flexible and form a fibre structure having relatively small capillaries when they are laid in a layer. An absorption layer consisting of CP fibres has a great ability to spread liquid; however, because the capillaries are small, absorption into the layer 15 only takes place slowly. In addition, the volume of liquid which can be absorbed into a structure consisting of CP fibres is relatively limited particularly since the fibres collapse when they are wetted. When the fibres collapse in this way, the fit of the product 1 can change drastically. The fit is understood as meaning the ability of the product 1 not to allow excreted liquid to leak out through openings or gaps which are formed by chance, for example in the crotch part, between the product 1 and the user's body. A good fit consequently minimizes leakage and the resulting problems in the form of soiled clothes, bedclothes or the like.

As a result of their properties being different, the two absorption layers 14,15 fulfill different functions. In this connection, the first absorption layer 14 serves as a layer for receiving the liquid which is imparted to the product 1. The first absorption layer 14 must be able rapidly to receive relatively large quantities of liquid over a short period of time, i.e. have great ability to absorb liquid instantaneously. In addition, the layer 14 must be able to retain the liquid until it is gradually absorbed by the second absorption layer 15. In this connection, the second absorption layer 15 constitutes a layer for storing and spreading the liquid. The liquid which is absorbed by the second absorption layer 15 is spread, through the capillary structure of the layer, away from the wetting region, i.e. the region of the layer which is the first to be wetted by the liquid. In this way, fresh liquid can gradually be taken up from the first absorption layer, i.e. from the first absorption layer 14 to the second absorption layer 15.

In order to ensure that the construction with two absorption layers 14,15 having different absorption properties will be able to be utilized in the manner intended, it is important that the liquid which is imparted to the product 1 is received by the first absorption layer 14 over a period of time which is as short as possible, i.e. that the absorption layer 14 has great ability to absorb liquid instantaneously. At the same time, it is important that the product 1 does not collapse, and provide a poor fit, after the product 1 has received liquid from the user.

In order to ensure that the first absorption layer 14 has as great an ability to absorb liquid instantaneously as possible, in accordance with the invention, two arcuate channels 16,17 have been constructed in the first absorption layer 14. In this connection, each of the two arcuate channels possesses two transverse end edges 18,19 and two longitudinal, curved side edges 20, 21 running between the end edges 18,19. The channels 16,17 extend through the whole of the thickness of the first absorption layer 14. The first transverse end edges 18 extend towards the first end part 7 of the product 1 while the second transverse end edges 19 extend towards the second end part 8 of the product 1. While the transverse end edges 18,19 are preferably rounded-off, they can alternatively assume other shapes, for example angular, pointed, asymmetrical or similar shapes. The two arcuate channels 16,17 are such that they to a certain extent follow the shape of the product 1, i.e. that the distance between the channels 16,17 is less at the narrower crotch part 9 of the product 1 than at the two end parts 7,8 of the product 1. In the embodiment of example shown, the two arcuate channels 16,17 are shorter lengthwise than is the first absorption layer 14.

The above description of the arcuate channels 16,17 is not, of course, limiting with regard to how the channels may be shaped. A number of other shapes, which are not shown on the drawing, are conceivable. Straight, oblique, angled or asymmetrical are only some examples of how the channels 16,17 may be shaped.

In order to ensure that the product 1 has as good a fit as possible, even after wetting, and a thin profile in accordance with the invention, a compressed area 22 has been constructed, mainly between the arcuate channels 16,17. Furthermore, the compressed area 22 possesses two transverse end edges 23 and two longitudinal, curved side edges 24 running between the end edges 23. While the transverse end edges 23 are preferably rounded-off, they can also assume shapes which are not shown on the drawing, for example angular, pointed, asymmetrical or similar shapes. While the curved side edges 24 preferably touch the outer, longitudinal, curved side edges 20 of the channels 16,17 in the transverse centre line of the product 1, they can also, in a manner not shown in the drawing, extend closer to the outermost edges of the first absorption layer 14 or, in a manner now shown in the drawing, extend closer to the centre line of the product. However, the compressed area 22 is smaller than the absorption layer 14. The compressed area 22 is shorter lengthwise than is the absorption layer 14. The compressed area 22 can be shorter, as long as, or longer than, the arcuate channels 16,17. The compressed area 22 is such that it to a certain extent follows the shape of the product 1, i.e. the distance between the curved side edges 24 is less at the narrower crotch part 9 of the product 1 than at the two end parts 7,8 of the product 1.

Figure 2A:
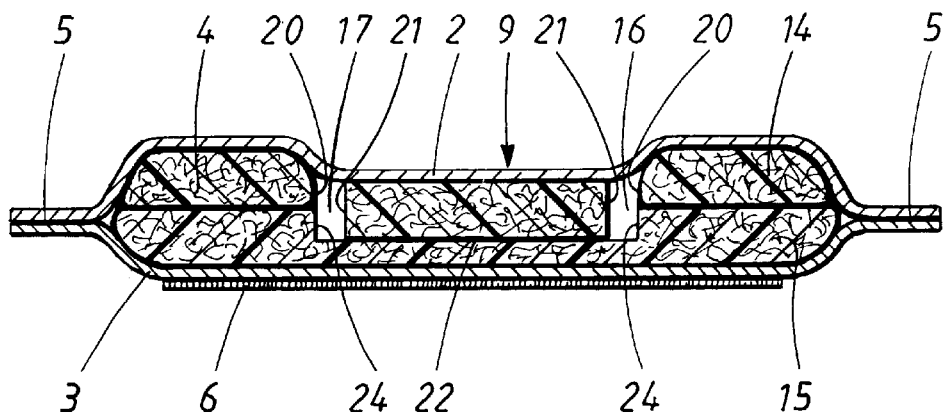
FIG. 2a shows a section through the absorbent product depicted in FIG. 1, with the section being taken along the line II—II and showing an absorption body in accordance with the first embodiment of the invention.
Figure 2B:
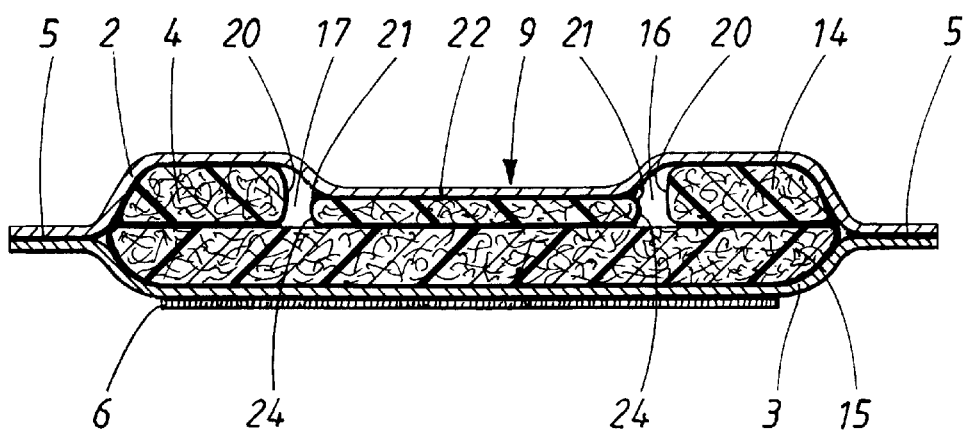
FIG. 2b shows a section through the absorbent product depicted in FIG. 1, with the section being taken along the line II—II and showing an absorption body in accordance with the second embodiment of the invention.

FIGS. 2a and 2b show two alternative structures for the absorption body 4 in the product 1 shown in FIG. 1. Thus, the absorption body 4 shown in FIG. 2a possesses a first absorption layer 14 and a second absorption layer 15 located between a liquid-permeable outer layer 2 and a liquid-impermeable backing layer 3. In the first absorption layer 14, there are two longitudinal, arcuate channels 16,17 which extend through the whole of the thickness of the first absorption layer 14. The absorption body 4 shown in FIG. 2a also possesses a second absorption layer 15 which is located between the first absorption layer 14 and the liquid-impermeable backing layer 3. The second absorption layer 15 has a compressed area 22 whose longitudinal side edges 24 preferably touch the outer edges 20 of the two channels 16,17 at the transverse centre line of the product 1. The longitudinal side edges 24 of the compressed area 22 can also, in a manner not shown in the drawing, extend closer to the longitudinal side edges of the product or extend closer to the longitudinal centre line of the product.

The absorption body 4 shown in FIG. 2b also possesses a first absorption layer 14 and a second absorption layer 15 located between a liquid-permeable outer layer 2 and a liquid-impermeable backing layer 3. There is furthermore, in the first absorption layer 14, a compressed area 22 which preferably touches the inner sides 21 of the channels 16,17 such that the longitudinal side edges 24 of the compressed area 22 coincide with the inner edges 21 of the channels 16,17 at the transverse centre line of the product 1. The longitudinal side edges 24 of the compressed area 22 can also extend closer to the longitudinal centre line of the product 1 at the transverse centre line of the product 1. The absorption body 4 shown in FIG. 2b also possesses a second absorption layer 15 which is located between the first absorption layer 14 and the liquid-impermeable backing layer 3.

Naturally, the embodiments shown in FIGS. 2a and 2b can be combined such that both the first and the second absorption layers 14,15 possess compressed areas 22 at the crotch part 9 of the incontinence protection.

What is claimed is:

1. An absorbent product having two longitudinal side edges (12,13), two transverse end edges (10,11), a longitudinal centre line and a transverse centre line, and which comprises a liquid-permeable outer layer (2), a liquid-impermeable backing layer (3) and an absorption core (4) which is located between said outer layer (2) and said backing layer (3), with said absorption core (4) comprising a first and a second absorption layer (14,15), with the first absorption layer (14) being arranged inside of the liquid-permeable outer layer (2) and the second absorption layer (15) being arranged between the first absorption layer (14) and the liquid-impermeable backing layer (3), with the first absorption layer (14) having two longitudinal channels (16,17), with each of the channels having an outer edge (20) closest to the corresponding longitudinal side edge (12,13) of the product and an inner edge (21) closest to the longitudinal centre line of the product, characterized in that the two longitudinal channels (16,17) extend through the whole of the thickness of the first absorption layer (14), in that a compressed area (22) is arranged between the longitudinal sides (12,13) of the absorbent product, and in that the distance between the side edges (24) of the compressed area (22) is smaller than or equal to the distance between the outer side edges (20) of the longitudinal channels (16,17).

2. Product according to claim 1, characterized in that the first absorption layer (14) consists of chemical thermomechanical pulp and in that the second absorption layer (15) consists of chemical pulp.

3. Product according to claim 1, characterized in that the first absorption layer (14) consists of chemical pulp and in that the second absorption layer (15) consists of chemical thermomechanical pulp.

4. Product according to claim 1, characterized in that the first absorption layer (14) is shorter in the longitudinal direction than is the second absorption layer (15).

5. Product according to claim 1, characterized in that the first absorption layer (14) is shorter in the transverse direction than is the second absorption layer (15).

6. Product according to claim 1, characterized in that the first absorption layer (14) is compressed between the outer edges (20) of the two longitudinal channels (16,17).

7. Product according to claim 1, characterized in that the second absorption layer (15) is compressed and in that the width of the compressed area (22) is smaller than or equal to the distance between the outer edges (20) of the two longitudinal channels (16,17).

8. Product according to claim 1, characterized in that the compressed area (22) consists of a separate layer.

9. Product according to claim 1, characterized in that the density of the area (22) of the compressed absorption layer is 0.1–0.5 g/cm$^3$.

10. Product according to claim 1, characterized in that at least one of the absorption layers (14,15) contains superabsorbents.

11. Product according to claim 1, characterized in that the longitudinal channels (16,17) are arcuate.

12. Product according to claim 1, characterized in that the length of each of the longitudinal channels (16,17) is 10–22 cm.

13. Product according to claim 1, characterized in that the distance between the inner edges (21) of each of the longitudinal channels (16,17) is 1.0–9.0 cm.

14. Product according to claim 1, characterized in that the distance between the outer and inner edge (20,21) of each of the longitudinal channels (16,17) is 0.1–1.0 cm.

15. Product according to claim 1, characterized in that at least one of the absorption layers (14,15) contains odour-inhibiting substrates.

16. Product according to claim 1, characterized in that the length of the compressed area (22) is 13–22 cm.

17. Product according to claim 1, characterized in that the distance between the side edges (24) of the compressed area (22) is 1–8 cm.

18. Product according to claim 1, characterized in that the second absorption layer (15) has two longitudinal arcuate channels and in that the channels extend through the whole of the thickness of the second absorption layer (15).

* * * * *